United States Patent

Bassi, Jr.

[11] Patent Number: 5,601,847
[45] Date of Patent: Feb. 11, 1997

[54] MICROBICIDES

[75] Inventor: Albert B. Bassi, Jr., High Point, N.C.

[73] Assignee: Ciba-Geigy Corporation, Tarrytown, N.Y.

[21] Appl. No.: 462,448

[22] Filed: Jun. 5, 1995

Related U.S. Application Data

[63] Continuation of Ser. No. 171,894, Dec. 21, 1993, abandoned, which is a continuation of Ser. No. 41,640, Apr. 1, 1993, abandoned.

[51] Int. Cl.$^6$ .......... A01N 37/12; A01N 37/44; A01N 59/20
[52] U.S. Cl. .......... 424/633; 424/638; 514/538
[58] Field of Search .......... 514/538; 424/633, 424/638

[56] References Cited

U.S. PATENT DOCUMENTS

| | | | |
|---|---|---|---|
| 4,151,299 | 4/1979 | Hubele | 424/309 |
| 4,742,079 | 5/1988 | Lambert et al. | 514/538 |
| 4,849,219 | 7/1989 | Staub et al. | 424/605 |
| 4,927,823 | 5/1990 | Gisi | 514/538 |

OTHER PUBLICATIONS

Research Disclosure 187(Nov. 1979) (3 pages).
Kocide 606 Flowable Label 4 pages (1980).
Champion Wettable Powder Label (4 pages) (1985).
Champ Flowable Label (4 pages) (1985).
Champion Technical Label (2 pages) Nov. 30, 1987.
Chemie der Pflanzenschutzund Schadlingsbekampfungsmittel, p. 47 (1970).
Worthing et al, The Pesticide Manual, 8th Ed. 11 533–534.
Kuczynska, C. A., vol. 116, (1992) 116: 146032x.

*Primary Examiner*—Allen J. Robinson
*Attorney, Agent, or Firm*—Marla J. Mathias; William A. Teoli, Jr.

[57] ABSTRACT

A microbicidal composition comprising metalaxyl and copper hydroxide exerts a synergistically potentiated activity against plant diseases, especially against metalaxyl-resistant pathogens. The active components may be applied in succession in any order or simultaneously.

18 Claims, No Drawings

MICROBICIDES

This is a continuation of Ser. No. 08/171,894, filed Dec. 21, 1993, abandoned, which is a continuation of Ser. No. 08/041,640, filed Apr. 1, 1993, abandoned.

The present invention relates to a microbicidal composition with enhanced synergistic activity against plant diseases and to a method of using such a composition.

The fungicidal acylaniline metalaxyl (N-(2,6-dimethylphenyl)-N-(methoxyacetyl) alanine) is described in U.S. Pat. No. 4,151,299 and has been shown to be highly effective in controlling Oomycetes, especially the downy mildew species (Peronosporales), and of preventing attack at the first onset. The great advantage of metalaxyl is its ability to penetrate into the plant cells and sap-flow and thus being able to protect in all parts against fungus attack or to prevent the spread of fungal growth at the onset of attack.

However, the exceedingly intensive use of metalaxyl over the past 15 years has led to the unexpectedly rapid growth of resistance to metalaxyl. For this reason, various protective fungicides have been proposed as mixture components for metalaxyl. Some of these mixtures are described in U.S. Pat. No. 4,849,219.

It has now been unexpectedly found that metalaxyl combined with copper hydroxide ($Cu(OH)_2$) exhibits synergistic results against fungus strains, particularly against fungus strains with diminished sensitivity to metalaxyl.

Accordingly, the present invention consists of a microbicidal composition comprising metalaxyl and copper hydroxide, which exerts a synergistically potentiated activity against plant diseases, especially against metalaxyl-resistant pathogens. The invention also relates to a method of controlling plant diseases which involves application of metalaxyl and copper hydroxide, in succession in any order or simultaneously, to a plant or locus thereof.

The combination of metalaxyl and copper hydroxide is particularly advantageous because it has been rated by the U.S. Environmental Protection Agency with an "E" classification (the safest oncongenicity rating).

The combination of metalaxyl and copper hydroxide has very useful curative, preventive and systemic properties for protecting cultivated plants. With this mixture it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms. This also applies to microorganisms that have developed resistance to metalaxyl.

The weight ratio of metalaxyl/copper hydroxide is preferably between about 1:2 and about 1:10. The particularly preferred ratio is between about 1:4 and about 1:8, with the most preferred ratio of about 1:6.

The combination is effective against the phytopathogenic fungi belonging to the following classes: Oomycetes (e.g. Pythium, Phytophthora, Peronospora, Albugo); Ascomycetes (e.g. Venturia, Podosphaera, Erysiphe, Monilinia, Uncinula); Basidiomycetes (e.g. the genera Hemileia, Rhizoctonia, Puccinia); Fungi imperfecti (e.g. Botrytis, Helminthosporium, Fusarium, Septoria, Cercospora, Alternaria and, especially, Pyricularia). In addition, metalaxyl has a systemic action. Thus, the combination can also be used as seed dressing agents for protecting seeds (fruit, tubers, grains) and plant cuttings against fungus infections as well as against phytopathogenic fungi which occur in the soil. The combination of the invention is especially well tolerated by plants and is ecologically non-harmful. Metalaxyl is degraded and its presence in the soil is no longer detectable after one growing season.

Without implying any limitation, target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marros, melons), fiber plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers).

The combination of the invention is normally applied in the form of compositions and can be applied to the crop area or plant to be treated, simultaneously or in succession, if desired together with further carriers, surfactants or application promoting adjuvants customarily employed in the art of formulation. Suitable carriers and adjuvants can be solid or liquid and correspond to the substances ordinarily employed in the formulation technology, e.g. natural or regenerated mineral substances, dispersants, wetting agents, tackifiers, thickeners, binders or fertilizers.

A preferred method of applying the metalaxyl and copper hydroxide combination is application to the growing parts of plants, especially the leaves (foliar application). The number of applications and the rate of application depend on the biological and climatic life conditions of the pathogen. However, the active components can also penetrate the plant through the roots via the soil (systemic action) by drenching the locus of the plant with a liquid formulation, or by applying the compounds in solid form to the soil, e.g. in granular form (soil application). The compound may also be applied to seeds (coating) by impregnating the seed either with a liquid formulation of one component or coating them with the combined formulation. In special cases, further types of application are also possible, e.g. selective treatment of the buds or fruit.

Metalaxyl and copper hydroxide are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering, coating or pouring, are chosen in accordance with the intended objectives and the prevailing circumstances. Advantageous rates of application are normally from 100 g to 4 kg a.i./ha, most preferably from 100 g to 2 kg a.i./ha.

The formulations are prepared in known manner, e.g. by homogeneously mixing and/or grinding the active ingredients with extenders, e.g. solid carriers and surface-active compounds (surfactants).

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or beutonite; and suitable nonadsorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. front animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Suitable surface-active compounds are nonionic, cationic and/or anionic surfactants having good emulsifying, dispersion and wetting properties. The term "surfactants" will also be understood as comprising mixtures of surfactants. A preferred wetting agent is butyl naphthalene sulfonate. A particularly preferred dispersing agent is Reax 100M made by Westvaco Chemical, which is a modified kraft lignin with a high sulfonic acid group content. This dispersing agent has been found to be particularly useful in the particular metalaxyl/copper hydroxide composition.

Furthermore, the present invention also embraces a method of treating plant diseases, which comprises applying the compounds of metalaxyl and copper hydroxide and the compositions containing them to the locus already infected or in danger of infection. The application of both compounds can be made in any order or simultaneously.

The following are examples of compositions according to the invention. The examples are for illustrative purposes only and are not in any way intended to limit the scope of the claims presented hereinafter.

EXAMPLE 1

The following ingredients are added to a blender and mixed for approximately 15 minutes.
10.0% by weight of metalaxyl,
60.0% by weight of copper hydroxide,
2.0% by weight of Sorbit BNS (butyl naphthalene sulfonate wetting agent made by Henkel Corp.),
4.0% by weight of Reax 100M (dispersant of modified kraft lignin with high sulfonic acid group content made by Westvaco Chemical),
14.0% by weight of Huber 90A (kaolin clay made by Huber Corp.), and
10.0% by weight of Hi Sil 233 (highly dispersed absorbent material made by PPG Corp., used as a grinding aid).

The unground product is led from the mixer to a grinding unit. The grinding of the product is accomplished using an impact or air mill. The wettable powder product is blended for approximately 15 minutes to ensure final homogeneity.

Five pounds of the wettable powder are packaged in a water-soluble polymer bag. The bag and its contents are dissolved into a sprayer or n-fix tank which is partially filled with at least 5 gallons of water. After vigorous agitation, additional water is added to reach the desired concentration.

EXAMPLE 2

For prevention against the downy mildew of cucurbit vegetables, the composition of Example 1 (between 1.5 to 2.0 lbs./acre of the pre-dissolved wettable powder) is applied before infection and continued at 14-day intervals until the threat of disease is over. A higher rate is used under severe disease pressure.

EXAMPLE 3

For control of Pythium spp. and *Phytophthora capsici* on peppers, 1.0 lb./acre metalaxyl is applied to the soil, followed by one supplemental application 30 days following the soil application. Thereafter, 4–5 foliar applications of the composition of Example 1 at a rate of 2.5 lbs. pre-dissolved wettable powder/acre are given at 10–14 day intervals.

EXAMPLE 4

The combination of the invention is used as a foliar fungicide in a preventive disease control program for control of late blight and tuber rot on potatoes caused by *Phytophthora infestans*, Pythium leak caused by Pythium spp., and pink rot caused by *Phytophthora ethroseptica*. For late blight, the composition of Example 1 (1.5 to 2.5 lbs./acre of the pre-dissolved wettable powder) is applied before infection and continued at 14-day intervals. For tuber rot, Pythium leak and pink rot, the composition of Example 1 (2.0 to 2.5 lbs./acre of the pre-dissolved wettable powder) is first applied at flowering and another application 14 days later. A third application is made 14 days after the second application if the field has a history of tuber disease problems.

EXAMPLE 5

For control of Oomycete fungi including cavity spot on carrots and white rust on radishes, 1.0–2.0 lbs./acre metalaxyl is applied to the soil at or before planting. Forty to fifty days after this application, the composition of Example 1 (2.0 lbs./acre of the pre-dissolved wettable powder) are applied, followed by 2–4 additional applications on a 14-day schedule.

EXAMPLE 6

For control of white rust and downy mildew on spinach, 1.0–2.0 lbs./acre metalaxyl is applied to the soil at planting. Forty to filly days after this application or immediately after each repeated cutting, the composition of Example 1 (2.5 lbs./acre of the pre-dissolved wettable powder) are applied foliarly, followed by 1–2 additional applications on a 14-day schedule.

EXAMPLE 7

For control of Phytophthora fruit rot (such as buckeye rot), late blight, bacterial speck and bacterial spot on tomatoes, the composition of Example 1 (between 1.5 and 2.5 lbs./acre of the pre-dissolved wettable powder mixture) is applied before infection and continued at 5–7-day intervals until the threat of disease is over. A higher rate is used under severe disease pressure.

EXAMPLE 8

Action against downy mildew (Pseudoperonospora) on cucumbers

Comparative tests as shown below were made with foliage application on cucumbers against Pseudoperonospora. Percentage infection was tested twenty-one days after first application.

| Test No. | Pounds/acre of active ingredient | | Infection |
|---|---|---|---|
| | Metalaxyl | Copper hydroxide | |
| 1 | 0.00 | 0.00 | 53.3% |
| 2 | 0.15 | 0.90 | 9.0% |
| 3 | 0.20 | 1.20 | 14.0% |
| 4 | 0.30 | 1.80 | 6.0% |
| 5 | 0.00 | 1.54 | 25.0% |

EXAMPLE 9

Action against downy mildew (Pseudoperonospora) on cantaloupe

Comparative tests as shown below were made with foliage application on cantaloupe against Pseudoperonospora. The first application was made 49 days after planting, and continued on 7-day schedule thereafter. Percentage infection was tested 70 and 77 days after first application.

| Test No. | Pounds/acre of active ingredient | | Infection | |
|---|---|---|---|---|
| | Metalaxyl | Copper hydroxide | Day 70 | 77 |
| 1 | 0.00 | 0.00 | 76% | 97% |
| 2 | 0.00 | 1.54 | 31% | 74% |
| 3 | 0.15 | 0.90 | 10% | 48% |
| 4 | 0.20 | 1.20 | 9% | 32% |

EXAMPLE 10

Action against downy mildew (Pseudoperonospora) on cucumbers

Comparative tests as shown below were made with foliage application on cucumbers against Pseudoperonospora. Three applications were made on a 7-day schedule. Percentage infection was tested thirty-three days after first application.

| Test No. | Pounds/acre of active ingredient | | Infection |
|---|---|---|---|
| | Metalaxyl | Copper hydroxide | |
| 1 | 0.00 | 0.00 | 49% |
| 2 | 0.00 | 1.54 | 29% |
| 3 | 0.15 | 0.90 | 19% |
| 4 | 0.20 | 1.20 | 20% |

EXAMPLE 11

Action against early blight (*Alternaria solani*) on tomatoes

Comparative tests as shown below were made with foliage application on tomatoes against *Alternaria solani*. Alternaria is not an Oomycete, and therefore metalaxyl is not efficacious alone. Percentage infection was tested twenty-one days after first application.

| Test No. | Pounds/acre of active ingredient | | Infection |
|---|---|---|---|
| | Metalaxyl | Copper hydroxide | |
| 1 | 0.00 | 0.00 | 8.500% |
| 2 | 0.00 | 1.54 | 0.525% |
| 3 | 0.15 | 0.90 | 0.500% |

EXAMPLE 12

Action against white rust (*Albugo occidentalis*) on spinach

Comparative tests as shown below were made with foliage application on spinach against *Albugo occidentalis*. Treatments were applied on a 14-day schedule, and percentage infection was tested twenty days after the first application.

| Test No. | Pounds/acre of active ingredient | | Infection |
|---|---|---|---|
| | Metalaxyl | Copper hydroxide | |
| 1 | 0.00 | 0.00 | 27.50% |
| 2 | 0.25 | 0.00 | 17.50% |
| 3 | 0.00 | 1.16 | 7.80% |
| 4 | 0.25 | 1.50 | 6.25% |

EXAMPLE 13

Action against downy mildew (Peronospora) on broccoli

Comparative tests as shown below were made with foliage application on broccoli against Peronospora. Five applications were made in total with a 14-day schedule. Percentage infection was tested 74 days after first application.

| Test No. | Pounds/acre of active ingredient | | Infection |
|---|---|---|---|
| | Metalaxyl | Copper hydroxide | |
| 1 | 0.00 | 0.00 | 25.0% |
| 2 | 0.00 | 1.54 | 16.3% |
| 3 | 0.20 | 1.20 | 12.5% |

It will thus be seen that the objects set forth above, among those made apparent from the preceding description, are efficiently attained and, since certain changes may be made in carrying out the above composition and in the method set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, n-fight be said to fall therebetween.

Particularly it is to be understood that in said claims, ingredients or compounds recited in the singular are intended to include compatible mixtures of such ingredients wherever the sense permits.

What is claimed is:

1. A foliage fungicidal composition efficacious against foliage plant pathogens consisting essentially of synergistic fungicidally effective amounts of metalaxyl and copper hydroxide in a weight ratio between about 1.2 and about 1.10.

2. The foliage fungicidal composition of claim 1, further comprising an agriculturally-acceptable carrier.

3. The foliage fungicidal composition of claim 2, wherein the agriculturally-acceptable carrier is a mineral filler.

4. The foliage fungicidal composition of claim 3, wherein the mineral filler is kaolin clay.

5. The foliage fungicidal composition of claim 2, further comprising at least one surfactant.

6. The foliage fungicidal composition of claim 5, wherein the surfactant includes a wetting agent and a dispersant.

7. The foliage fungicidal composition of claim 6, wherein the wetting agent is butyl naphthalene sulfonate.

8. The foliage fungicidal composition of claim 6, wherein the dispersant is a modified kraft lignin with a high sulfonic acid group content.

9. The foliage fungicidal composition of claim 1, wherein the weight ratio is between about 1:4 and about 1:8.

10. The foliage fungicidal composition of claim 9, wherein the weight ratio is about 1:6.

11. A method of controlling foliage pathogens on a plant, which method comprises treating the plant with a synergistic fungicidally effective amount of a foliage fungicidal composition consisting essentially of metalaxyl and copper hydroxide in a weight ratio between about 1.2 and 1:10.

12. The method of claim 11, wherein the plant is treated first with metalaxyl and subsequently with copper hydroxide.

13. The method of claim 11, wherein the plant is treated first with copper hydroxide and subsequently with metalaxyl.

14. The method of claim 11, wherein the plant is treated simultaneously with metalaxyl and copper hydroxide.

15. The method of claim 11, wherein the amount of composition is 100 g to 4 kg metalaxyl and copper hydroxide per ha.

16. The method of claim 15, wherein the amount of composition is from 100 g to 2 kg per ha.

17. The method of claim 11, wherein the plant disease is selected from the group consisting of Pseudoperonospora, Pythium spp., *Phytophthora capsici, Phytophthora infestans, Phytophthora ethroseptica, Albugo occidentalis, Plasmopara viticola* and Phytophthora fruit rot.

18. The method of claim 11, wherein the plant is selected from the group consisting of cucurbit vegetables, peppers, potatoes, carrots, radishes, grapes, cole crops, leafy vegetables and tomatoes.

* * * * *